United States Patent
Sun (10) Patent No.: US 8,420,708 B2
(45) Date of Patent: Apr. 16, 2013

(54) METHODS FOR MAKING DENTAL RESTORATIONS USING TWO-PHASE LIGHT-CURING MATERIALS

(75) Inventor: Fuming Sun, Middletown (DE)

(73) Assignee: DENTSPLY International Inc., York, PA (US)

(*) Notice: Subject to any disclaimer, the term of this patent is extended or adjusted under 35 U.S.C. 154(b) by 0 days.

(21) Appl. No.: 13/079,864

(22) Filed: Apr. 5, 2011

(65) Prior Publication Data

US 2011/0183298 A1 Jul. 28, 2011

Related U.S. Application Data

(63) Continuation of application No. 12/072,263, filed on Feb. 25, 2008, now Pat. No. 7,939,575.

(60) Provisional application No. 60/903,089, filed on Feb. 23, 2007.

(51) Int. Cl.
| | |
|---|---|
| *C08F 2/48* | (2006.01) |
| *C08F 2/50* | (2006.01) |
| *G03F 7/029* | (2006.01) |
| *A61F 2/00* | (2006.01) |
| *A61C 5/08* | (2006.01) |

(52) U.S. Cl.
USPC ...... 522/4; 522/48; 522/64; 522/28; 523/115; 433/222.1

(58) Field of Classification Search ........ 522/4, 48, 522/64, 28; 523/115; 433/222.1
See application file for complete search history.

(56) References Cited

U.S. PATENT DOCUMENTS

| | | | |
|---|---|---|---|
| 4,131,729 A | 12/1978 | Schmitt et al. | |
| 4,389,497 A | 6/1983 | Schmitt et al. | |
| 4,737,593 A | 4/1988 | Ellerich et al. | |
| 4,771,084 A | 9/1988 | Kubota et al. | |
| 5,472,991 A | 12/1995 | Schmitt et al. | |
| 5,756,559 A | 5/1998 | Blackwell et al. | |
| 5,936,006 A | 8/1999 | Rheinberger et al. | |
| 6,008,264 A | 12/1999 | Ostler et al. | |
| 6,191,191 B1 * | 2/2001 | Harada et al. | 523/115 |
| 6,313,191 B1 | 11/2001 | Blackwell | |
| 6,386,865 B1 | 5/2002 | Suh et al. | |
| 6,387,981 B1 | 5/2002 | Zhang et al. | |
| 6,515,191 B2 | 2/2003 | Lal et al. | |
| 6,593,395 B2 | 7/2003 | Angeletakis et al. | |
| 6,783,810 B2 | 8/2004 | Jin et al. | |
| 6,866,506 B2 | 3/2005 | Plank et al. | |
| 6,964,985 B2 | 11/2005 | Karim et al. | |
| 7,494,339 B2 | 2/2009 | Dias et al. | |
| 7,767,731 B2 | 8/2010 | Chen et al. | |
| 2006/0229377 A1 | 10/2006 | Bublewitz et al. | |
| 2007/0148623 A1 | 6/2007 | Dias et al. | |
| 2008/0220396 A1 | 9/2008 | Sun | |
| 2009/0270528 A1 * | 10/2009 | Bowman et al. | 523/116 |

FOREIGN PATENT DOCUMENTS

| | | |
|---|---|---|
| DE | 03801511 A1 | 1/1988 |
| DE | 19617931 A1 | 4/1996 |
| EP | 0166009 A1 | 1/1986 |
| EP | 0325266 A2 | 7/1989 |
| EP | 0803240 A2 | 4/1997 |
| WO | 2007016508 A1 | 2/2007 |

* cited by examiner

*Primary Examiner* — Ling Choi
*Assistant Examiner* — Jessica E Whiteley
(74) *Attorney, Agent, or Firm* — David A. Zdurne; Douglas J. Hura; Leana Levin (57) ABSTRACT

Methods for making dental crowns, bridges, inlays, onlays, veneers, fillings, and other restorations are provided. The methods involve using a two-phase light curing (TPLC) material. Preferably, the TPLC material used to form the dental restoration comprises a blend of polymerizable compounds; photopolymerization systems (a) and (b), and particulate filler materials (a) and (b). In a first light-curing step, curing light having a wavelength of greater than 420 nm is used to activate system (a). In a second light-curing step, curing light having a wavelength of less than 420 nm is used to activate system (b). The two step light-curing method is efficient and allows the dentist to make restorations having high mechanical strength and pleasing aesthetics.

17 Claims, 2 Drawing Sheets

Figure 1: Curing Efficiency Comparison with >400 nm Light Exposure

Figure 2: Curing Efficiency Comparison with <400 nm Light Exposure

METHODS FOR MAKING DENTAL RESTORATIONS USING TWO-PHASE LIGHT-CURING MATERIALS

CROSS-REFERENCE TO RELATED APPLICATIONS

This is a continuation application of U.S. patent application Ser. No. 12/072,263 having a filing date of Feb. 25, 2008, now U.S. Pat. No. 7,939,575 which claims the benefit of U.S. Provisional Patent Application Ser. No. 60/903,089 having a filing date of Feb. 23, 2007, the entire contents of which are hereby incorporated by reference.

BACKGROUND OF THE INVENTION

1. Field of the Invention

The present invention relates generally to methods for making dental restorations such as fillings, crowns, bridges, inlays, onlays, and veneers. The method involves curing a photopolymerizable composition in two separate steps. The composition can be referred to as a two-phase light curing (TPLC) material.

2. Brief Description of the Related Art

Dental professionals make and use different restorations depending upon the condition of the tooth and oral health of the patient. By the term, "restoration" as used herein, it is meant any product that replaces or restores lost tooth structure, teeth, or oral tissue including, but not limited to, fillings, inlays, onlays, veneers, crowns, bridges, splints, and dentures.

In dental anatomy, the outer (visible) portion of the tooth is referred to as the crown and it has a covering of enamel. The hard enamel protects softer dentin tissue in the upper portion of the tooth. The dentin tissue contains a matrix of minute tubules interspersed with collagen fibers that surround and protect the tooth pulp. The pulp includes connective tissue, blood vessels, cells, and nerve endings. The pulp cavity comprises an upper pulp chamber and root canals that extend to the apex or apical section of the tooth deeper into the jaw. The outer (non-visible) portion of the tooth root is covered with cementum, a thin hard tissue that joins the root to the surrounding bone. Dental decay, or caries, is caused by bacteria accumulating on teeth and forming a biofilm (plaque). The biofilm produces acids that dissolve and weaken the tooth, thereby causing decay.

When dental caries is found in the enamel portion, the dental professional will remove the caries to prevent further decay of the tooth. The dentist uses a high-speed handpiece equipped with a bur to "drill" the tooth. Then, the cavity is "filled" with a composite resinous material or silver amalgam filling. In recent years, composite fillings which can be made to closely match the shade of neighboring teeth have become more popular than amalgam fillings.

Composite filling material typically contains photopolymerizable resins such as an acrylate or methacrylate resin, reinforcing filler particles such as silica and glasses, polymerization initiators, polymerization accelerators, and various additives such as ultraviolet-light absorbers, anti-oxidants, plasticizers, and the like. The composite can be light-cured using a standard dental curing light (for example, Smart-Lite™ PS LED curing light, available from Dentsply) to form a hardened dental restoration. The curing light normally emits blue visible light in the spectrum of 400 to 500 nm to activate the polymerization initiator. The monomers undergo polymerization and the filling material hardens. In some instances, it is desirable to light-cure the composition in two successive steps. In the first light-curing step, the composition is partially-cured. The dental practitioner can work with the composition shaping and molding it as needed while in the partially-cured state. When ready, the practitioner light-cures the material a second time so that it fully cures and forms a hardened restoration.

For example, Schmitt et al., U.S. Pat. No. 5,472,991 discloses tooth filling compositions that are curable in two curing steps. The composition comprises polymerizable compounds such as monomeric and polymeric acrylates and methacrylates; filler materials such as silica particles; photoinitiator component I having a light absorption maximum of <450 nm such as bisacylphosphine oxides; and photoinitiator component II having a light absorption maximum of >450 nm such as camphorquinone. The composition is irradiated with light having a wavelength of >450 nm in a partial curing step to form a material having between 50 to 70% of its maximum hardness and then it is irradiated with light at a wavelength of <450 nm so that it completely cures.

As discussed above, a filling is placed in the tooth if the tooth structure has enough strength and integrity to hold the filling. A filling can be placed in different areas of the tooth, for example, the occlusal and/or mesial and/or distal portions and these fillings are rated as Class I to Class VI restorations depending upon the location and condition of the tooth. In some cases, however, the tooth structure has weakened considerably and it is unable to hold a filling. In these cases, a different restoration must be made for the tooth. For example, a dental crown can be placed over the tooth to restore the anatomy, function, and aesthetics of the natural tooth.

In conventional dental crown procedures, a patient must make multiple visits to the dentist. In the first visit, the dentist examines and prepares the tooth that will receive the crown. The dentist "preps" the tooth by filing and grinding it to a core. Next, the dentist takes an impression of the prepared tooth. The final impression is sent to a dental laboratory that will make the permanent crown. During the first office visit, the dentist places a temporary crown on the tooth to cover and protect it while the permanent crown is being fabricated. The temporary crown is made from a polymeric paste-like material such as an acrylic. At the second office visit, the dentist removes the temporary crown. The dentist cleans the tooth removing any residual temporary cement. Then, the color, margins, contacts, and occlusal fit of the permanent crown are checked. If satisfactory, the dentist affixes the permanent crown to the tooth using permanent dental cement.

This crown fabrication procedure, which involves making multiple visits to the dentist, can be time-consuming and costly. In recent years, there have been efforts to find new techniques whereby a dentist could design and fabricate the crown "chair-side" and mount the crown on the patient's tooth in a single office visit.

For example, Dias et al., US Patent Application Publication US 2007/0148623 discloses a method for making a dental crown in a single office visit. The method involves applying a spacer material to the patient's prepared tooth structure and then placing a transparent, plastic matrix containing the composite crown-forming material over the tooth. Because the matrix is transparent, light can be irradiated through the matrix and onto the composite material. This causes the material to polymerize and form a crown. The hardened crown is removed from the tooth; finished and polished; and then permanently mounted on the tooth using permanent dental cement. This chair-side technique for making a dental crown in a single office is a promising development. However, there is a need for an improved crown-forming material and method. The '623 Publication does not disclose a photopolymerizable composition containing two different photoinitiators and mixture of filler materials that could be cured in two distinct light-curing steps.

There is a need in the dental field for an improved restorative composition that can be cured in two separate and distinct light-curing steps. A dental practitioner should be capable of using the composition to make restorations having high mechanical strength and pleasing aesthetics. In addition, the composition should have good working time so that the dental practitioner can handle and place the material more effectively. The present invention provides such compositions having these benefits as wells as other advantageous properties. Methods of using the compositions to make chair-side dental crowns and other restorations such as chair-side inlays, onlays, veneers, and fillings are also included.

SUMMARY OF THE INVENTION

This invention provides methods of making dental restorations such as fillings, inlays, onlays, veneers, crowns, bridges, splints, and dentures using a two-phase light-curing composition. The photopolymerizable composition includes polymerizable compounds such as monomers and polymers of acrylates and methacryaltes; photopolymerization system (a) containing a photoinitiator having a light absorbency maximum wavelength of greater than 420 nm; photopolymerization system (b) containing a photoinitiator having a light absorbency maximum wavelength of less than 420 nm; and a mixture of structural fillers and nanofillers.

In a first light-curing step, the composition is exposed to light having a having a wavelength of greater than 420 nm—this activates photopolymerization system (a) so that the composition partially-cures. In a second light-curing step, the composition is exposed to light having a wavelength of less than 420 nm—this activates photopolymerization system (b) and the composition fully cures. The polymerization systems may contain different photoinitiators, accelerators, and photopolymerization inhibitors.

For example, in one preferred formulation, photopolymerization system (a) comprises camphorquinone and ethyl 4-(dimethylamino)benzoate, and photopolymerization system (b) comprises 2,4,6-trimethylbenzoyl-diphenyl-phosphine oxide. In another preferred version, photopolymerization system (a) comprises camphorquinone and ethyl 4-(dimethylamino)benzoate, and photopolymerization system (b) comprises 2-benzyl-2-(dimethylamino)-4'-morpholinobutyrophenone. Butylated hydroxytoluene can be used as a photopolymerization inhibitor in both preferred formulations.

The mixture of structural filler and nanofiller materials provides the restoration with high mechanical strength and pleasing aesthetics. In one preferred version, the structural filler comprises fluoride barium boron aluminosilicate glass particles and the nanofiller comprises fumed silica particles.

DETAILED DESCRIPTION OF THE PREFERRED EMBODIMENTS

The present invention relates to methods of producing dental restorations using a two-phase light-curing (TPLC) material. Preferably, the TPLC material comprises a blend of polymerizable compounds; photopolymerization systems (a) and (b); and particulate filler materials (a) and (b).

Polymerizable Compounds

The polymerizable compounds used in TPLC material are capable of being cured or hardened to form a polymer network. The polymerizable compounds have sufficient strength and hydrolytic stability with low toxicity so that they are safe for human use.

One class of suitable polymerizable compounds contains materials having free radically active functional groups and includes monomers, oligomers, and polymers having one or more ethylenically unsaturated groups. Such free radically polymerizable compounds include, but are not limited to, mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,6-hexanediol di(meth)acrylate, pentaerythritol triacrylate, pentaerythritol tetraacrylate, pentaerythritol tetramethacrylate, sorbitol hexacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA); polyurethane dimethacrylate (PUDMA); alkoxylated pentacrythritol tetraacrylatel; polycarbonate dimethacrylate (PCDMA); the bis-acrylates and bis-methacrylates of polyethylene glycols; copolymerizable mixtures of acrylated monomers; acrylated oligomers; acidic monomers such as dipentaerythritol pentacrylate phosphoric acid ester (PENTA); and bis[2-(methacryloxyloxy)-ethyl]phosphate. Mixtures of the above-described polymerizable compounds can be used. The polymerizable compounds are typically present in the TPLC material in an amount in the range of about 10% to about 60% by weight and more preferably in the range of 20% to 50% by weight based on weight of composition.

In addition to the foregoing polymerizable compounds, the materials may contain diluent, polymerizable monomers, such as for example, hydroxy alkyl methacrylates, ethylene glycol methacrylates, and diol methacrylates such as tri(ethylene glycol)dimethacrylate (TEGDMA) to reduce the composition's viscosity and make it more suitable for application inside of the mouth.

Photopolymerization System (a)

The TPLC material further includes a photopolymerization system (a), which is capable of being activated by visible light having a wavelength in the range of about 400 to about 550 nm.

The photopolymerization system (a) includes a photoinitiator for example, benzophenone, benzoin and their derivatives or alpha-diketones and their derivatives. A particularly preferred photoinitiator is camphorquinone (CQ) compound. Preferably, photopolymerization system (a) is activated by irradiating the composition with blue, visible light preferably having a wavelength in the range of about 420 to about 530 nm. The CQ compound has a light absorbency range of between about 420 to about 500 nm and generate free radicals for polymerization when irradiated with light having a wavelength in this range. The maximum absorbency range of the CQ compounds is about 460 to about 475 nm.

The photopolymerization system (a) is preferably present in the TPLC composition in the range of about 0.005 to about 0.5 wt. % and more preferably in the range of about 0.01 to about 0.025 wt. % based on weight of polymerizable compounds. The photoinitiator (e.g., CQ compound) of photopolymerization system (a) is preferably present in the TPLC composition in the range of about 0.005 to about 0.035 wt. % based on weight of polymerizable compounds. Photopolymerization system (a) further includes a polymerization accelerator, which is preferably a tertiary amine. One example of a suitable tertiary amine is ethyl 4-(dimethylamino)benzoate (EDAB). Other tertiary amines may be used such as, for example, triethanol amine; N,N,3,5, tetramethyl aniline; 4-(dimethylamino)-phenethyl alcohol; dimethyl aminobenzoic acid ester; dimethyl-p-toluidine; dihydroxyethyl-p-toluidine; hydroxyethyl-p-toluidine; and the like. The polymerization accelerator is preferably present in the composition in the range of about 0.05 to about 0.5 wt. % and more preferably in the range of about 0.1 to about 0.3 wt. %, based on weight of polymerizable compounds.

Photopolymerization system (a) is activated in a first light-curing step and photopolymerization system (b) is activated in a second light-curing step. Various light sources can be used to effectively expose the composition to curing light and activate photopolymerization systems (a) and (b) as discussed further below. Standard Light-Emitting Diode (LED) curing lights or halogen curing lights equipped with filter systems may be used to activate photopolymerization system (a) in this first light-curing step. Suitable LED dental curing lights include, for example, those sold under the brand names: SmartLite™ PS and iQ2 (Dentsply); Elipar™ (3M Espe); L.E. Demetron II™ (Kerr); and Bluphase™ (Ivoclar Vivadent). The SmartLite™ iQ2 curing light has a spectral emission of about 420 to about 530 nm. If a halogen curing light is used, it is equipped with a filtering system to prevent the transmission of undesired wavelengths of light. For example, the filtering system may allow only light at a desired blue wavelength (e.g., >420 nm) to pass through so that it is directed onto the light-curable composition. The photosensitive (CQ) compounds are excited at this wavelength and generate free radicals to initiate polymerization. That is, photopolymerization system (a) is fully activated. Meanwhile, the undesirable light wavelengths (e.g., <420 nm) are deflected by the filters back into the housing of the curing light. As a result, photopolymerization system (b), which is discussed further below, is not activated.

One advantage of the TPLC composition used in this invention is that it contains a relatively small amount of CQ compound. Using such a small amount of CQ compound means that less free radicals will be generated and only partial polymerization of the material will occur during the first light-curing step. The TPLC composition is only partially hardened in this phase so the practitioner can continue to work with and shape the material in the tooth if needed. Another advantage with using such a small amount of CQ compound is that it can be combined with a relatively small amount of reducing agent (polymerization accelerator) such as EDAB as discussed above. Using a CQ/EDAB photopolymerization system in accordance with this invention results in partial curing as opposed to complete curing during the first curing step. The practitioner thus has extended working time to mold and carve the material. The TPLC composition does not harden completely until photopolymerization system (b) is fully activated in a second light-curing step.

Photopolymerization System (b)

The TPLC material further includes a photopolymerization system (b), which is capable of being activated by visible light having a wavelength in the range of about 360 nm to about 450 nm.

The photopolymerization system (b) includes, but is not limited to, acylphosphine oxides such as monoacyl phosphine oxide derivatives, bisacyl phosphine oxide derivatives, triacyl phosphine oxide derivatives, a aminoketone, benzyldimethyl ketal and their derivatives acting as photoinitiators. The photopolymerization system (b) is preferably present in the TPLC composition in the range of about 0.01 to about 0.5 wt. % and more preferably in the range of about 0.05 to about 0.025 wt. % based on weight of polymerizable compounds. The photoinitiator (e.g., acylphosphine oxide) of photopolymerization system (b) is preferably present in the TPLC composition in the range of about 0.05 to about 0.10 wt. % based on weight of polymerizable compounds. In a preferred embodiment, 2,4,6-trimethylbenzoyl-diphenyl-phosphine oxide (LTPO) is used as the initiator in photopolymerization system (b). The LTPO compounds have a light absorbency maximum of between about 360 to about 410 nm and generate free radicals for polymerization when irradiated with light having a wavelength in this range. When the TPLC material is irradiated with light in this spectrum, the composition fully cures and hardens to form the finished restoration.

As discussed above, a standard LED curing light with a spectral emission of 420 to 530 nm may be used in the first curing phase. Alternatively, a halogen curing light equipped with a filtering system may be used. In the first light-curing phase, only photopolymerization system (a) is fully activated. In the second curing phase, a halogen curing light, which does not contain a filtering system, or a dental curing oven, can be used.

If a LED curing light is used in the first curing phase, then a standard halogen curing light, which does not contain a filtering system, such as Spectrum™ 800 halogen light (Dentsply) can be used in the second curing phase. The Spectrum™ 800 curing light has a spectral emission range of about 350 to about 530 nm. On the other hand, if a halogen curing light containing a filtering system (e.g., one that blocks transmission of light at wavelengths of <420 nm) is used in the first curing phase, the filtering system must first be removed and the light made ready for second phase curing. After removing the filtering system, the halogen curing light is powered on and the composition is exposed again to light radiation. Because the filtering system has been removed, light at wavelengths across the emission spectrum (that is, less than and greater than 420 nm) is emitted and directed onto the composition. As a result, photopolymerization system (b) is fully activated. In addition, any residual amount of non-activated photoinitiator (a) is activated upon exposing the composition to this broad spectral light. It is recognized that as an alternative to using dental curing lights, a standard dental curing oven can be used to irradiate the composition and activate photopolymerization system (b) in the second curing phase. Suitable dental curing ovens include, for example, those sold under the brand names: Triad® 2000™ Visible Light Curing Unit (Dentsply) and Enterra™ VLC Curing Unit (Dentsply).

Also, it is contemplated that LED curing lights, which do not use a filtering system, also could be used in the methods of this invention. For example, Plank et al., U.S. Pat. No. 6,866,506 discloses a curing light having multiple LED chips. The LED chips are organized into groups which are commonly actuated. Each group is controlled by a dedicated control device operating independently of the control device for the other groups. The LED chips of the first group have an emission maximum of 470 nm and the LED chips of the second group have an emission maximum of 420 nm. This LED curing light, having a broad light-emission spectrum, with a control system for activating and deactivating certain LEDs, could be suitable for light-curing the TPLC composition of this invention.

In addition, the TPLC composition may include a polymerization inhibitor such as, for example, butylated hydroxytoluene (BHT); hydroquinone; hydroquinone monomethyl ether; benzoquinone; chloranil; phenol; butyl hydroxyanaline (BHA); tertiary butyl hydroquinone (TBHQ); tocopherol (Vitamin E); and the like. Preferably, BHT is used as the polymerization inhibitor. The polymerization inhibitors act as scavengers to trap free radicals in the resulting composition and to extend the working and setting time of the composition. The polymerization inhibitors prevent the composition from curing too rapidly. The polymerization inhibitors are typically present in the composition in the range of about 0.01 to about 2 wt. % based on weight of polymerizable compounds. The composition may include one or more polymerization inhibitors.

Particulate Filler

The TPLC material further includes a mixture of particulate filler (a) and (b). Reinforcing particulate filler (a) has an average particle size of greater than 100 nm (0.1 μm) and less than 1000 nm (1.0 μm). That is, particulate filler (a) is sub-micron sized, but it should not be considered nanometer-sized. The powdered particulate (a) comprises discrete and individual particles that are not substantially agglomerated or aggregated. The particles are characterized by having a relatively small particle size and large surface area. The particulate filler (a) can be considered a structural filler. By the term, "structural filler" as used herein, it is meant particulate filler having an average particle size of greater than 100 nm (0.1 μm) and less than 1000 nm (1.0 μm). In one preferred version, the structural filler has an average particle size in the range of about 0.35 to about 0.95 μm. The concentration of structural filler in the composition is generally in the range of about 30 to about 90 wt. % based on weight of the composition.

On the other hand, the particulate filler (b) has an average particle size of less than 100 nm (0.1 μm) and preferably has a size in the range of 1 to 50 nm (0.001 to 0.05 μm). That is, the particles comprising particulate filler (b) are nanometer-sized—they can be referred to as nanoparticles or nanofillers. By the term, "nanofiller" as used herein, it is meant particulate filler having an average particle size of greater than 1 nm (0.001 μm) and less than 100 nm (0.1 μm). In one preferred version, the nanofiller has an average particle size in the range of about 20 nm (0.02 μm) to about 40 nm (0.04 μm).

The organically modified silica or organically modified silicate nanoparticles diluted in various unsaturated (meth-)acrylate resins such as Ormosil II (available from Dentsply) and colloidal silica sols dispersed in various unsaturated (meth-)acrylate binding agents such as Nanocryl® (available from Hanse Chemie AG) are particularly preferred. These materials can be generally referred to as filler systems having colloidal silica particles dispersed within methacrylate or acrylate resins. In general, the concentration of nanofiller in the TPLC composition is normally in the range of about 1 to about 30 weight percent based on weight of the composition.

The particulate filler materials (a) and (b) are dispersed homogenously and uniformly throughout the resin matrix. The dispersed particles may come into contact with each other, but they generally do not form agglomerates or clusters. It is important that a blend of structural fillers and nanofillers be used in the composition of this invention as opposed to some photocurable compositions containing two photoinitiators such as those described in the above-mentioned Schmitt et al., U.S. Pat. No. 5,472,991. The compositions described in the '991 patent preferably contain silica particles having an average particle size of 0.02 to 0.05 μm and finely divided inorganic particles having an average particle size of 1 to 15 μm such as pigmented quartz having a particle size of about 6 μm. The pigmented quartz or other finely divided inorganic particles are not sub-micron sized.

In the instant invention, the mixture of sub-micron sized structural fillers and nanometer-sized nanofillers helps to make the composition stronger while maintaining aesthetics. The composition can be used to make a restoration having high mechanical strength and pleasing aesthetics. The finished restoration has a smooth surface and glossy appearance. Moreover, the surface smoothness and luster of the finished restoration is durable. The restoration can withstand toothbrush abrasive forces without its surface roughness increasing dramatically. Because the patient will chew and bite on the finished restoration, it is important that the restoration has good mechanical strength. In addition to their good aesthetics, the restorations made with the compositions of this invention show high fracture-resistance and compressive strength. The finished restorations will not wear away easily when subject to mastication forces.

The particulate filler materials (a) and (b) may include inorganic fillers which can be naturally-occurring or synthetic. Such materials include, but are not limited to, silica, titanium dioxide, iron oxides, silicon nitrides, glasses such as calcium, lead, lithium, cerium, tin, zirconium, strontium, barium, and aluminum-based glasses, borosilicate glasses, strontium borosilicate, barium silicate, lithium silicate, lithium alumina silicate, kaolin, quartz, talc, and mixtures thereof. The glasses may or may not have fluoride-releasing properties. The benefits of using fluoride-releasing glasses are well known. Such materials are capable of releasing fluoride into the oral cavity over the long term. Fluoride generally provides added protection against acid attack that can cause tooth decay. Mixtures of the above-described filler materials also can be used in the composition if desired. Organic particles such as polycarbonates and polyepoxides also can be used as the filler materials.

In one preferred composition, structural particulate (a) consisting of fluoride barium boron aluminosilicate glass (FBAG) particles having an average particle size of about 0.94 μm (for example, EG 9726 glass particles available from Ferro Corp) is mixed with nanofiller particulate (b) consisting of fumed silica particles having an average particle size of about 0.02 μm (for example, Aerosil 9200 available from DeGussa AG). In this composition, the concentration of FBAG particles is in the range of about 30 to about 90 wt. % based on total weight of the composition. And, the concentration of nanofillers is in the range of about 1 to about 20 wt. %.

In a second preferred version, structural particulate (a) consisting of FBAG glass particles having an average particle size of about 0.94 μm is mixed with nanofiller particulate (b) consisting of fumed silica particles having an average particle size of about 0.04 μm (for example, OX-50 available from DeGussa AG) and a colloidal dispersion of 50 wt. % amorphous silica having an average particle size of 0.02 μm in TEGDMA resin (for example, Nanocryl D301 available from Hanse Chemie AG). In this composition, the concentration of FBAG particles is in the range of about 30 to about 90 wt. % based on total weight of the composition. And, the concentration of nanofillers is in the range of about 1 to about 20 wt. %.

In a third preferred version, structural particulate (a) consisting of a blend of: (i) FBAG particles having an average particle size of about 0.94 µm and (ii) strontium glass (STG) particles having an average particle size of about 0.4 µM (for example, G018-093 glass particles available from Schott Electronic Packaging, Inc.) is blended with nanofiller particulate (b) consisting of fumed silica particles having an average particle size of about 0.04 µm (for example, OX-50) and organically modified silica nanoparticles having an average particle size of 0.002 to 0.003 µm dispersed in (meth-) acrylate resin (for example, Ormosil II available from Dentsply). In this composition, the concentration of FBAG particles having an average particle size of about 0.94 µm is in the range of about 30 to about 70 wt. % and STG particles having an average particle size of about 0.4 µm is in the range of about 10 to about 30 wt. % based on total weight of the composition. The concentration of nanofillers is in the range of about 1 to about 20 wt. % based on total weight of the composition. As described in the above second and third preferred versions, using the Nanocryl D30 or Ormosil filler systems provides the composition with improved handling and mechanical strength properties as well as reduced polymerization shrinkage.

The particles of both particulate filler materials (a) and (b) can be surface-treated with silane compounds or other coupling agents so that they can be more uniformly dispersed within the resin matrix. Suitable silane compounds include, but are not limited to, gamma-methacryloxypropyltrimethoxysilane, gamma-mercaptopropyltriethoxysilane, gamma-aminopropyltrimethoxysilane, and combinations thereof.

Additives

The TPLC material also can include additives to provide specially desired properties. For example, fluoride-releasing agents; flavorants; pigments; fluorescent agents; opalescent agents; ultra-violet stabilizers; anti-oxidants; viscosity modifiers, and the like can be added to the TPLC formulation.

Methods

The above-described TPLC material can be used to make different dental restorations. In one method, a dentist can use the TPLC material to make a dental crown chair-side in a single office visit.

Using this chair-side method, a dentist first takes a pre-operative impression or matrix of the patient's teeth including the tooth that will receive the crown. The dentist preferably uses a transparent plastic tray that is filled with a polyvinyl siloxane (PVS) impression material or other suitable impression material. It is important that the tray be transparent, because curing light is transmitted through the tray in a subsequent step of the process as discussed in further detail below. The dentist presses the plastic tray containing the silicone material on the surface of the teeth to form the impression. After the impression has been formed in the silicone material, the dentist removes the tray from the mouth. The resulting impression is an accurate negative likeness of the teeth anatomy.

The dentist next prepares the tooth that will receive the crown using conventional crown-prep techniques. Then, the dentist places layers of the TPLC material into the impression (or matrix) of the tooth, which will receive the crown, beginning with the enamel layer. Next, the dentin layer is injected into the impression. The dentist takes care that the correct amount of TPLC material is placed in the impression. If a sufficient amount of TPLC material is not introduced, gaps will form in the resulting crown and there will be occlusion problems. On the other hand, if too much TPLC material is introduced, there also may be occlusion problems. For example, the crown may sit too high. The dentist carefully customizes the shade of the TPLC material so that it matches the color of the patient's teeth.

After the dentist has filled the hardened impression with the TPLC crown-forming material, it is inserted into the patient's mouth. The TPLC material is molded over the prepared tooth so that it forms a crown for the tooth. Then, the shaped TPLC material is partially-cured and hardened in a first light-curing step. By the term, "partially-cured" as used herein, it is meant the composition is cured so that the crown can be removed from the mouth easily but it is strong enough to prevent plastic deformation.

A standard Light-Emitting Diode (LED) curing light or halogen curing light with a filter which only allows light having a wavelength >420 nm to pass through may be used to partially-cure the TPLC material as described above. Since the plastic tray containing the TPLC material is transparent, the curing light is able to pass through and partially-cure the material. In this first light-curing phase, the photopolymerization system (a), which contains, for example, the CQ and EDAB compounds, is activated. The CQ compound has a light absorbency range of between about 420 to about 500 nm and generate free radicals for polymerization when irradiated with light having a wavelength in this range. The composition thus begins to harden and form a crown structure.

Next, the dentist removes the partially-cured crown from the tooth. The dentist may use an explorer, probe, crown remover, or other suitable instrument to detach the crown. Under ordinary circumstances, the dentist would have difficulty removing the crown from the tooth. However, because the material is only partially-cured at this point, the dentist is able to remove the crown easily. The partially-cured TPLC material does not have full hardness and does not strongly adhere to the surface of the tooth. Still, the TPLC material has sufficient hardness and stability such that the shape and integrity of the crown is maintained. There is no plastic deformation of the partially-cured crown.

After removing the crown, the dentist trims excess flush material and then fully cures the crown in a second light-curing step as discussed above. A halogen dental curing light or light-curing oven may be used to fully cure the TPLC material. The curing light or oven needs to be capable of emitting light at a wavelength <420 nm to activate photopolymerization system (b). Halogen light sources can emit light across a broad spectrum of wavelengths. CQ/EDAB photo-initiators generally require light having a wavelength of about 420 to about 500 nm to be triggered. Halogen lights, or light curing ovens, with their broad spectral light output, can trigger photoinitiators other than CQ/EDAB compounds. In this second light-curing phase, the photopolymerization system (b), which, for example, contains the LTPO compound, is activated. The LTPO compound has a light absorbency maximum of between about 360 to about 410 nm and generates free radicals for polymerization when irradiated with light having a wavelength in this range.

After completing this second light-curing step, the crown is ready to be permanently affixed to the tooth. The crown can be finished with burs and polished using customary crown-finishing methods as the dentist believes is necessary. A sealant, which provides a stain-resistant and glossy surface finish, may be applied to the crown. Then, the finished crown is permanently affixed to the tooth using permanent cement. Conventional permanent cements, as known in the dental industry, may be used in this step. By following these techniques, a crown or other dental restoration can be made "chair-side." The crown has good aesthetic properties and mechanical strength.

It should be understood that the above-described method is directed to making dental crowns for illustration purposes only. The method can be used to make other dental restorations such as, for example, bridges, inlays, onlays, veneers, and fillings.

As discussed above, one of the key advantages of the TPLC composition used in this invention is that it provides the practitioner with extended working time in making the restoration. The TPLC composition is only partially hardened in the first light-curing phase. By controlling curing time, the partially-cured material can have a soft, wax-like consistency so it can be nicely carved and shaped. The practitioner can use standard dental instruments such as condensers, pluggers, and carvers to shape and reshape the partially hardened material. The flowability of the material (prior to any curing steps) makes it particularly suitable for direct restoratives. The partial curing of the material leaves it in a highly moldable condition so it can be carved and shaped in detail to provide a restoration having good margins, contacts, and occlusal fit. This shaping and reshaping occurs prior to the second curing step, whereby the restoration becomes fully hardened.

The present invention is further illustrated by the following Examples, but these Examples should not be construed as limiting the scope of the invention.

EXAMPLES

The following is a list of compounds used to make the compositions described in the Examples.

| Abbreviations of Compounds: | |
|---|---|
| Bis-GMA | Bisphenol A dimethacrylate |
| EBPADMA | Ethoxylated (2) bisphenol A dimethacrylate |
| UDMA | Urethane dimethacrylate |
| P&PII | Photo polymerizable resin |
| Ormosil II | Organically modified silica nano particles diluted with EBPADMA |
| Nanocryl D301 | Colloidal dispersion of 50 wt % amorphous silica in TEGDMA |
| TEGDMA | Triethyleneglycol dimethacrylate |
| SR454 | Ethoxylated (3) trimethylolpropane triacrylate |
| SR444 | Pentaerythritol Triacrylate |
| Uvinul M40 | Oxybenzone |
| BHT | Butylated hydroxytoluene |
| CQ | Camphorquinone |
| EDAB | 4-ethyl dimethylaminobemzoate |
| LTPO | Lucirin TPO |
| MBF | Methybenzoylformate |
| MMTMPP | 2-Methyl-4'-(methylthio)-2-morpholinopropiophenone |
| BDMBP | 2-Benzyl-2-(dimethylamino)-4'-morpholinobutyrophenone |
| EG9726 | Fluoride barium boron aluminosilicate glass filler |
| G018-093 | Strontium glass filler |
| Aerosil 9200 | Silanated fumed silica filler |
| Ox-50 | Fumed silica filler |
| FS | Flexural Strength |
| FM | Flexural Modulus |
| CS | Compressive Strength |
| DTS | Diametral Tensile Strength |

Example 1

Several photopolymerizable resin blends were prepared by dissolving certain amount of photoinitiators in a resin blend comprising 69.97 parts by weight of P&PII, 10 parts EBPADMA, 15 parts TEGDMA and 5 parts SR454 and 0.03 parts BHT under mechanical stirring at 50° C. for one hour until a homogeneous solution was obtained. The different compositions of photoinitiators used in the resin blends are described in Table 1.

TABLE 1

Photoinitiator Content (parts by weight).

| Sample ID | CQ | EDAB | LTPO | MBF | MMTMPP | BDMAP |
|---|---|---|---|---|---|---|
| RB-1 | 0.01 | 0.03 | 0.50 | | | |
| RB-2 | 0.02 | 0.10 | 0.25 | | | |
| RB-3 | 0.02 | 0.10 | 0.50 | | | |
| RB-4 | 0.02 | 0.10 | | 0.50 | | |
| RB-5 | 0.02 | 0.10 | | | 0.50 | |
| RB-6 | 0.02 | 0.10 | | | | 0.50 |

The curing activity of the photopolymerizable resin blends was studied by using a Photo DSC (TA Instruments DSC 2920). About 20-30 mg of each sample was placed in the Al pan and cured for 5 minutes with commercially available long and short wavelength curing light using <400 nm and >400 nm cut-off filters, respectively, the light intensity is about 200 mw. The curing efficiency of the activated resin blends with the two-wavelength exposure is demonstrated in FIGS. 1 and 2 below.

Figure 1:
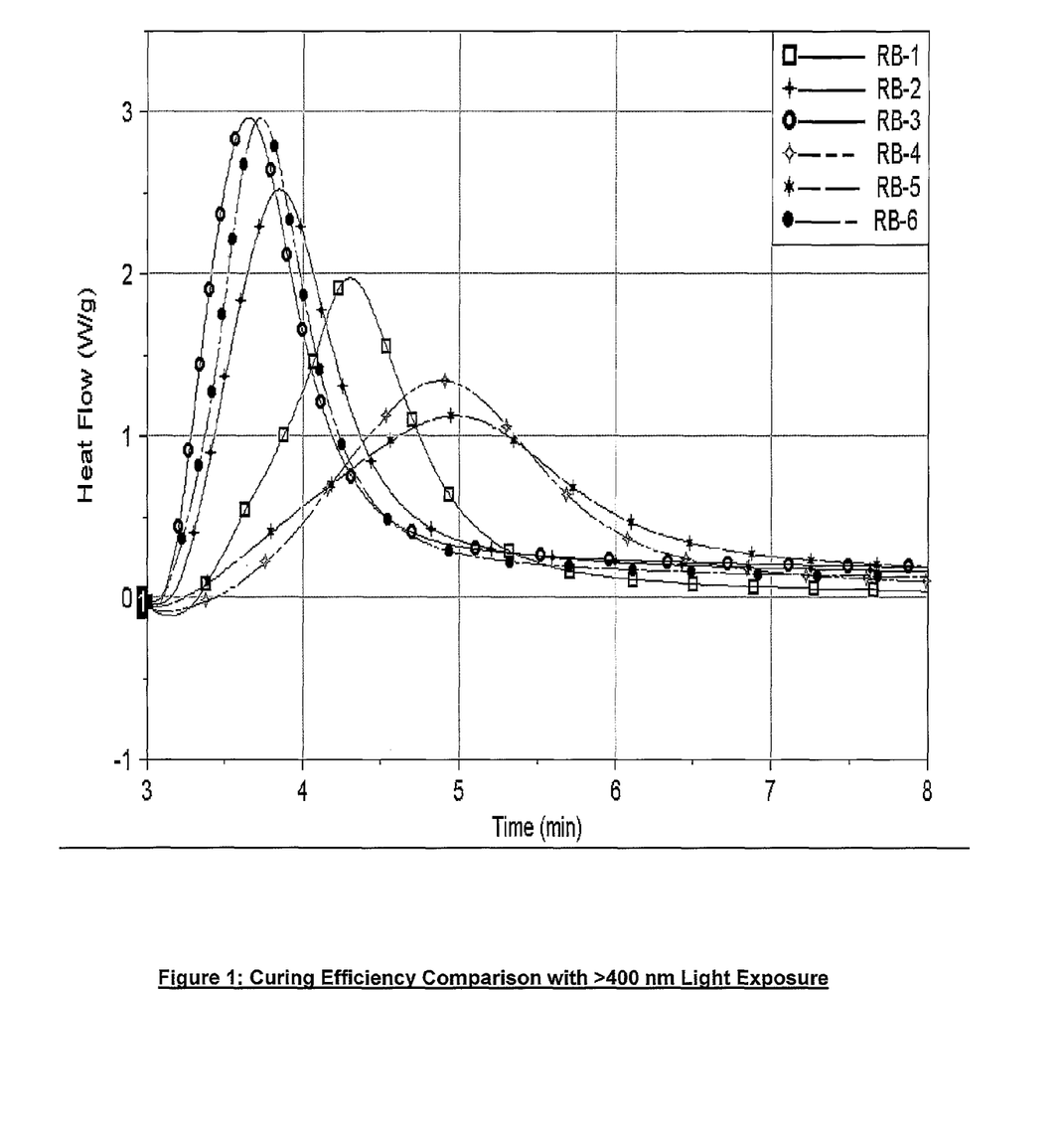
FIG. 1 is a graph showing the curing efficiency of various photoinitiator blends upon exposure to curing light at wavelengths greater than 400 nm.
Figure 2:
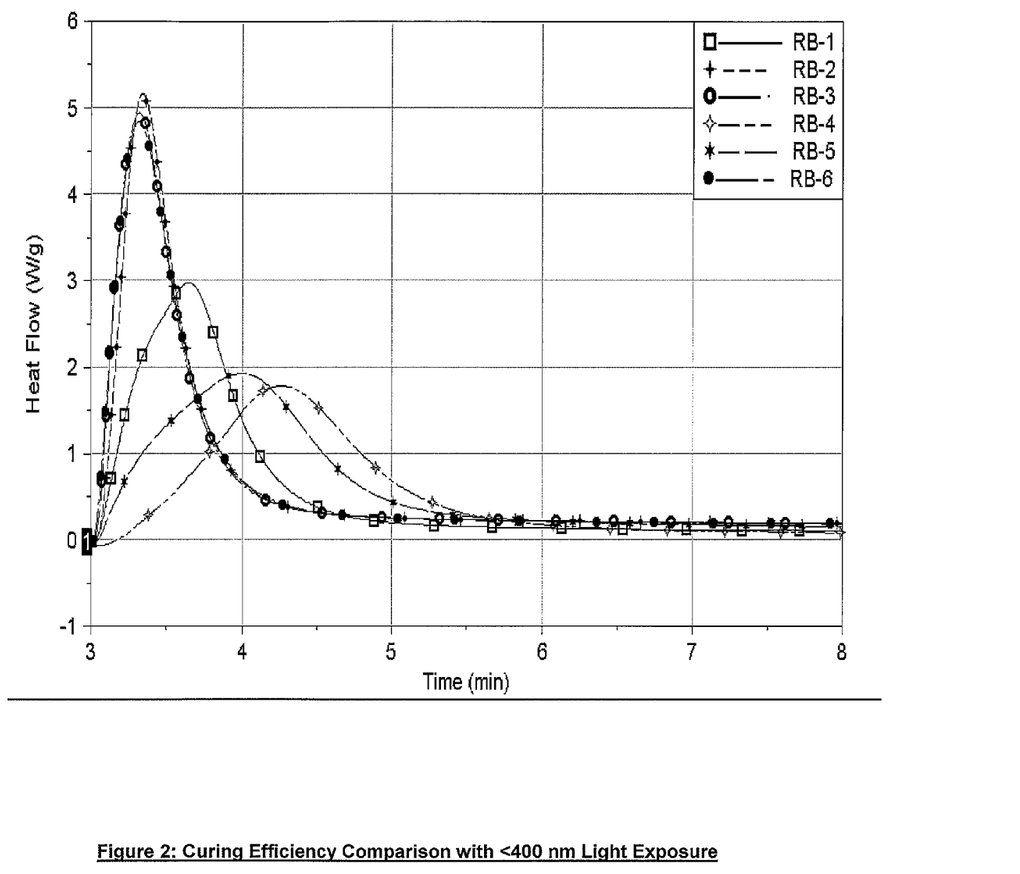
FIG. 2 is a graph showing the curing efficiency of various photoinitiator blends upon exposure to curing light at wavelengths less than 400 nm.

Resin blends RB-2, RB-3 and RB-6 exhibited good curing efficiency with curing light exposure at both wavelights.

Example 2

A resin composite was prepared by adding 73 parts by weight of silanated EG9726 and 2 parts Aerosil 9200 to 25 parts of RB-2 resin blend—the paste was prepared by mixing 2 minutes using SpeedMixer at room temperature followed by vacuum in a Ross Mini Mixer for 20 minutes under mixing at 50° C.

The resin composite was cured for certain time periods with SmartLite™ iQ2 LED curing light (Dentsply), the hardness of the partially-cured material was measured immediately and at 15 seconds interval after curing. There are several standard methods used to measure hardness, but the most common method is Barcol Hardness. In this method, a carbide steel pin penetrates the material under a specific loading force. The Barcol hardness is specified as a function of the penetration depth of the pin. The results are reported in Table 2 below.

TABLE 2

Barcol Hardness vs LED Curing Time and Post-Curing Time.

| Cure time (seconds) | Barcol Hardness (measured at 15 second intervals) | | | | | | | | |
|---|---|---|---|---|---|---|---|---|---|
| | 0 | 15 | 30 | 45 | 60 | 75 | 90 | 105 | 120 |
| 5 | 12 | 56 | 62 | 66 | 62 | 70 | 70 | 71 | 71 |
| 10 | 68 | 78 | 80 | 80 | 80 | 82 | 85 | 85 | 84 |
| 15 | 76 | 85 | 85 | 85 | 86 | 87 | 87 | 87 | 88 |
| 20 | 82 | 83 | 86 | 85 | 87 | 85 | 87 | 86 | 87 |

For comparison, the Barcol hardness of commercial TPH®3 micro matrix restorative composite (Dentsply) reached 90 after 5 seconds of curing with the LED light under the same conditions.

The resin composite in Example 2 was tested for chairside crown fabrication using a Viade typodont. The paste was filled into the hardened transparent impression matrix then the matrix filled with the paste was molded over the prepared tooth so that it formed a crown for the tooth. The crown was easy to remove and trim after 20 seconds curing with the iQ2 LED curing light through the transparent matrix (1$^{st}$ phase). The final crown presented excellent fit to the prepared tooth after being fully cured (2$^{nd}$ phase) for 2 minutes with a Triad® 2000™ curing oven or 20 seconds on each side with a Spectrum® 800 halogen curing light (Dentsply). The crown was also easily removed from the prepared tooth when the 2$^{nd}$ cure was conducted using Spectrum® 800 halogen light for 20 seconds on each side with crown sit on the prepared tooth.

Example 3

Also analogously to Example 2, another resin composite was prepared by adding 69 parts silanated EG9726 and 6 parts of silanated Ox-50 to 25 parts of resin blend consisting of 10.99 parts of Bis-GMA, 2.75 parts of EBPADMA, 2.96 parts of UDMA, 5.92 parts of Nanocryl D301, 1.97 parts of SR444, 0.25 parts of Uvinul M40, 0.005 parts of CQ, 0.025 parts of EDAB, 0.125 parts of LTPO and 0.0075 parts of BHT.

Example 4

Analogously to Example 2, a resin composite was prepared by adding 48 parts of silanated EG9726, 24 parts of silanated of G018-093 and 3 parts of silanated Ox-50 to 25 parts of resin blend consisting of 6.66 parts of Bis-GMA, 7.89 parts of Ormosil II, 4.87 parts of UDMA, 3.70 parts of TEGDMA, 1.48 parts of SR454, 0.25 parts of Uvinul M40, 0.005 parts of CQ, 0.025 parts of EDAB, 0.125 parts of LTPO and 0.0075 parts of BHT.

Resin composites Example 3 and Example 4 were tested for chairside crown fabrications, and both materials exhibited excellent handling performance.

The mechanical properties of the cured composites were tested with Instron. The specimens prepared from cured pastes were soaked in deionized water at 37° C. at least overnight before polishing to the proper sizes. The cylindrical specimen for the compressive mode measures 4 mm×6 mm, while the specimen for the diametral test measures 6 mm×3 mm. Both flexural strength and flexural modulus were determined by subjecting a 2 mm×2 mm×25 mm rectangular sample of the material to three-point bending as outlined in the ISO 4049 test method. In Table 3, the mechanical properties of resin composites of Example 2, 3 and 4 are compared with the commercial TPH®3 dental composite.

TABLE 3

Comparison of Mechanical Properties.

| Sample ID | FS (MPa) | FM (MPa) | CS (MPa) | DTS (MPa) |
|---|---|---|---|---|
| TPH ® 3 | 133 (4) | 8963 (284) | 392 (19) | 53.5 (4.4) |
| Example 2 | 142 (8) | 7790 (157) | 339 (12) | 52.5 (2.3) |
| Example 3 | 150 (10) | 10018 (467) | 399 (11) | 56.0 (3.2) |
| Example 4 | 133 (10) | 9062 (319) | 391 (19) | 47.2 (5.9) |

The results show that the TPLC resin composites of the present invention had comparable mechanical properties to TPH®3 restorative while the use of Nanocryl D301 filled resin in the resin blend improved Flexural strength and modulus of the resultant material.

What is claimed is:

1. A method of making a dental restoration, comprising the steps of:
   a) providing a two-phase light-curing composition, the composition comprising:
      (i) about 10 to about 60% by weight of polymerizable compound based on the composition,
      (ii) about 0.005 to about 0.5% by weight of photopolymerization system (a) based on the polymerizable compound, the photopolymerization system (a) containing a photoinitiator having a light absorbency maximum wavelength of greater than 420 nm,
      (iii) about 0.05 to about 0.5% by weight of photopolymerization system (b) based on the polymerizable compound, the photopolymerization system (b) containing a photoinitiator having a light absorbency maximum wavelength of less than 420 nm,
      (iv) about 30 to about 90% by weight of structural filler based on the composition, the structural filler has an average particle size in the range of about 0.35 to about 0.95 μm; and
      (v) about 1 to about 30% by weight of nanofiller based on the weight of the composition, the nanofiller has an average particle size in the range of about 0.02 to about 0.04 μm;
   b) dispensing the two-phase light-curing composition into a substantially transparent plastic matrix;
   c) placing the plastic matrix in a mouth of a patient so that the composition is molded over the tooth surface;
   d) irradiating the composition with light having a wavelength of greater than 420 nm to activate photopolymerization system (a) so that the composition partially-cures to form a restoration;
   e) removing the hardened restoration from the surface of the tooth; and
   f) irradiating the composition with light having a wavelength of less than 420 nm to activate photopolymerization system (b) so that the composition fully cures; and
   wherein photopolymerization system (a) comprises camphorquinone, ethyl 4-(dimethylamino)benzoate and butylated hydroxytoluene; and photopolymerization system (b) comprises 2,4,6-trimethylbenzoyl-diphenyl-phosphine oxide.

2. The method of claim 1, wherein the polymerizable compound is selected from the group consisting of acrylate, methacrylates, and mixtures thereof.

3. The method of claim 1, wherein the composition comprises polymerizable compounds selected from the group consisting of ethoxylated bisphenol A-dimethacrylates, tri (ethylene glycol)dimethacrylate, and pentaerythritol triacrylate, and mixtures thereof.

4. The method of claim 1, wherein the structural filler is fluoride barium boron aluminosilicate glass particles and the nanofiller is fumed silica particles.

5. The method of claim 1, wherein the structural filler is a blend of fluoride barium boron aluminosilicate glass particles and strontium glass particles and the nanofiller is fumed silica particles.

6. The method of claim 1, wherein the structural filler and nonfillers are surface-treated with silane compounds.

7. The method of claim 1, wherein the nanofiller is a filler system having colloidal silica particles dispersed within a methacrylate or acrylate resin.

8. The method of claim 1, wherein the dental restoration is selected from the group consisting of crowns, bridges, inlays, onlays, veneers, and fillings.

9. The method of claim 1, wherein the nanofiller is a filler system having colloidal silica particles dispersed within a methacrylate or acrylate resin.

10. The method of claim 1, further comprising the steps of finishing and polishing the restoration and permanently affixing the restoration to the tooth using permanent dental cement.

11. The method of claim 1, wherein the photopolymerization system (a) is present in an amount of about 0.01 to about 0.025 by wt % of the polymerizable compound and the photopolymerization system (b) is present in an amount of about 0.05 to about 0.025 by wt % of the polymerizable compound.

12. The method of claim 11, wherein:
  (i) the composition comprises polymerizable compounds selected from the group consisting of ethoxylated bisphenol A-dimethacrylates, tri(ethylene glycol) dimethacrylate, and pentaerythritol triacrylate, and mixtures thereof; and
  (ii) the structural filler is a blend of fluoride barium boron aluminosilicate glass particles and strontium glass particles and the nanofiller is fumed silica particles.

13. The method of claim 1, wherein the composition comprises polymerizable compounds including Bis-GMA and ethoxylated bisphenol A-dimethacrylate.

14. The method of claim 1, wherein the composition comprises polymerizable compounds including ethoxylated bisphenol A-dimethacrylate and urethane dimethacrylate.

15. The method of claim 1, wherein the composition comprises polymerizable compounds including ethoxylated bisphenol A-dimethacrylate and trimethylolpropane triacrylate.

16. The method of claim 1, wherein the composition comprises polymerizable compounds including urethane dimethacrylate and trimethylolpropane triacrylate.

17. The method of claim 1, wherein the composition comprises polymerizable compounds including Bis-GMA, ethoxylated bisphenol A-dimethacrylate, urethane dimethacrylate, and trimethylolpropane triacrylate.

* * * * *